United States Patent
Holloway et al.

(10) Patent No.: US 6,262,234 B1
(45) Date of Patent: Jul. 17, 2001

(54) NUCLEAR RECEPTOR POLYPEPTIDE ZPPAR4

(75) Inventors: James L. Holloway; Laura J. Jelinek; Diane M. Durnam; Hal Blumberg, all of Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/106,194

(22) Filed: Jun. 26, 1998

Related U.S. Application Data

(60) Provisional application No. 60/051,032, filed on Jun. 27, 1997.

(51) Int. Cl.[7] ................ C07K 14/72; C07K 14/705; C07K 14/47; C07K 14/435
(52) U.S. Cl. ........................... 530/350; 435/69.1
(58) Field of Search ................ 530/350; 435/69.1

(56) References Cited

PUBLICATIONS

Evans, *Science* 24: 889–895, 1988.
Becker–Andre' et al., *Biochem. Biophys. Res. Comm. 194*: 1371–1379, 1993.
Becker–Andre' et al., *J. Biol. Chem. 269*: 28531–28534, 1994.
Carlberg et al., *Mol. Endocrinol. 8*: 757–770, 1994.
Forman et al., *Mol. Endocrinol. 8*: 1253–1261, 1994.
Hirose et al., *Biochem. Biophys. Res. Comm. 205*: 1976–1983, 1994.
Bourguet et al., *Nature 375*: 377–382, 1995.
Kliewer et al., *Cell 83*: 813–819, 1995.
Lehmann et al., *J. Biol. Chem. 270*: 12953–12956, 1995.
Steinhilber et al., *J. Biol. Chem. 270*: 7037–7040, 1995.
Wiesenberg et al., *Nuc. Acids Res. 23*: 327–333, 1995.
Carlberg & Wiesenberg, *J. Pineal Res. 18*:171–178, 1995.
Missbach et al., *J. Biol. Chem. 271*: 13515–13522, 1996.
Becker–Andre' & Delamarter, *Biochem. Biophys. Res. Comm. 194*: 1371–1379, 1993, RATRZRB.
Sikela, Human cDNAs from Infant Brain, 1994, EST 76096.
Auffray et al., *C.R. Acad. Sci. III, Sci. Vie 318*: 263–72, 1995.
Becker–Andre', Direct Genbank Submission, Aug. 6, 1997, HSTFAC.
Becker–Andre', Direct Genbank Submission, Aug. 6, 1997, GGTFAC.
TIGR Tentative Human Consensus, THC202869, Jul. 3, 1997.

*Primary Examiner*—Michael Pak
(74) *Attorney, Agent, or Firm*—Susan Lingenfelter

(57) ABSTRACT

The present invention relates to ZPPAR4 polynucleotide molecules and ZPPAR4 polypeptide molecules. ZPPAR4 is a novel member of the nuclear receptor superfamily. The novel ZPPAR4 nuclear receptor can be used to examine ZPPAR4-related complex transcriptional networks and biological processes. The disclosed ZPPAR4 polynucleotides and polypeptides provide a means to identify the natural ligand for ZPPAR4, as well as agonists and antagonists thereof.

2 Claims, 1 Drawing Sheet

```
                          1          15 16         30 31          45 46          60
1 ROR2_HUMAN    ---------------- ---------------- ---------------- ----------------      0
2 RZRB_RAT      ---------------- ---------------- ---------------- ----------------      0
3 ppar4pcrcontig -LTIGLERPPGQVSL AAPFLPVTEQ-KFTL  WIR-QAQMSCENAHA  LPSTPPFFLFFLFPF      57

61          75 76         90 91         105 106         120
1 ROR2_HUMAN    ---------------- ---------------- ---------------- ----------------      0
2 RZRB_RAT      ---------------- ---------------- ---------------- ----------------      0
3 ppar4pcrcontig FPLVPSPSSL-LTKP PPTPPPAAALPPPPQ  SK-SQKKSSEPEAVA  FFKKQAHWRERKRKT    115

121         135 136        150 151        165 166         180
1 ROR2_HUMAN    ---MNEGAPGDSDLE  TEARVPWSIMGHCLR  TGQARMSATPTPAGE  GARRDELFGILQILH     57
2 RZRB_RAT      ---------------- ---------------- ---------------- ----------------      0
3 ppar4pcrcontig KPKQNPGTRQPEHFF FTLPENKQTNKQSSK  QSPPTSKLLT-RRRR  QTSPCSHGVRLKGWF    174

181         195 196        210 211        225 226         240
1 ROR2_HUMAN    QCILSSGDAFVLTGV  CCSWRQNGKPPYS-Q  KEDKEVQTGY-MNAQ  IEIIPCKICGDKSSG    115
2 RZRB_RAT      ---------------- -RDFWVLWGSGWE-L  HDYTEQDSGHIMRAQ  IEVIPCKICGDKSSG     43
3 ppar4pcrcontig SRQSSSSPTTFFTRA ERDFWALRGSGWEQL  HDYAERESGHTMRAQ  IEVIPCKICGDKSSG    234

241         255 256        270 271        285 286         300
1 ROR2_HUMAN    IHYGVITCEGCKGFF  RRSQQSNATYSCPRQ  KNCLIDRTSRNRCQH  CRLQKCLAVGMSRDA    175
2 RZRB_RAT      IHYGVITCEGCKGFF  RRSQQNNASYSCPRQ  RNCLIDRTNRNRCQH  CRLQKCLALGMSRDA    103
3 ppar4pcrcontig IHYGVITCEGCKGFF RRSQQNNASYSCPRQ  RNCLIDGTNRNRCQH  CRLQKCLALGMSRDA    294

301         315 316        330 331        345 346         360
1 ROR2_HUMAN    VKFGRMSKKQRDSLY  AEVQKHRMQQQQRDH  QQQPGEAEPLTPTYN  IS-ANGLTELHDDLS    234
2 RZRB_RAT      VKFGRMSKKQRDSLY  AEVQKHQ-QRLQEQR  QQQSGEAEALARVYS  SSISNGLSNLNTETG    162
3 ppar4pcrcontig VKFGRMSKKQRDSLY AEVQKHQ-QRLQEQR  QQQSGEAEALARVYS  SSISNGLSNLNNETS    353

361         375 376        390 391        405 406         420
1 ROR2_HUMAN    N-YIDGHTPEGSKAD  SAVSSFYLDIQPSPD  QSGLDING---IKPE  PICDYTPASGFFPYC    290
2 RZRB_RAT      GTYANGHVIDLPKSE  G--YYNIDSGQPSPD  QSGLDMTGIKQIKQE  PIYDLTSVHNLFTYS    220
3 ppar4pcrcontig GTYANGHVIDLPKSE G--YYNVDSGQPSPD  QSGLDMTGIKQIKQE  PIYDLTSVPNLFTYS    411

421         435 436        450 451        465 466         480
1 ROR2_HUMAN    SFTNGETSPTVSMAE  LEHLAQNISKSHLET  CQYLREELQQITWQT  FLQEEIENYQNKQRE    350
2 RZRB_RAT      SFNNGQLAPGITMSE  IDRIAQNIIKSHLET  CQYTMEELHQLAWQT  HTYEEIKAYQSKSRE    280
3 ppar4pcrcontig SFNNGQLAPGITMTE IDRIAQNIIKSHLET  CQYTMEELHQLAWQT  HTYEEIKAYQSKVLW    471

481         495 496        510 511        525 526         540
1 ROR2_HUMAN    VMWQLCAIKITEAIQ  YVVEFAKRIDGFMEL  CQNDQIVLLKAGSLE  VVFIRMCRAFDSQNN    410
2 RZRB_RAT      ALWQQCAIQITHAIQ  YVVEFAKRITGFMEL  CQNDQILLLKSGCLE  VVLVRMCRAFNPLNN    340
3 ppar4pcrcontig ETMRKFFCDYPIAVL LKLSTIGMLHWAILF  CKGILQIVRYLPASL  ALPTRCAIALTHTCD    531

541         555 556        570 571        585 586         600
1 ROR2_HUMAN    TVYFDGKYASPDVFK  SLGCEDFISFVFEFG  KSLCSMHLTEDEIAL  FSAFVLMSADRSWLQ    470
2 RZRB_RAT      TVLFEGKYGGMQMFK  ALGSDDLVNEAFDFA  KNLCSLQLTEEEIAL  FSSAVLISPDRAWLL    400
3 ppar4pcrcontig NQKCLQILPTVSKEA KLPLKNHCPIVTTET  VPSSNDFRTSLADFL  GGGKEQEQCNNHSSC    591

601         615 616        630 631        645 646         660
1 ROR2_HUMAN    EKVKIEKLQQKIQLA  LQHVLQKNHREDGIL  TKLICKVSTLRALCG  RHTEKLMAFKAIYPD    530
2 RZRB_RAT      EPRKVQKLQEKIYFA  LQHVIQKNHLDDETL  AKLIAKIPTITAVCN  LHGEKLQVFKQSHPD    460
3 ppar4pcrcontig NRHKLTQQIYGTRLS KVFSCPACKESKKQD  NSSHIFIITLCHFFG  FVEEVFKRNLLLFFS    651

661         675 676        690 691        705 706         720
1 ROR2_HUMAN    IVRLHFPPLYKELFT  SEFEPAMQIDG----  ----     556
2 RZRB_RAT      IVNTLFPPLYKELFN  PDCAAVCK-------  ----     483
3 ppar4pcrcontig IYITLLWDRDPQLQN PPVDGTLIKYINVTC  PGGRSSPI 689
```

Figure

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 2094 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

-continued

```
TAACTCACTA TAGGGCTCGA GCGGCCGCCC GGGCAGGTCT CTCTCGCTGC TCCCTTCCTC      60

CCTGTAACTG AACAGTGAAA ATTCACATTG TGGATCCGCT AACAGGCACA GATGTCATGT     120

GAAAACGCAC ATGCTCTGCC ATCCACACCG CCTTTCTTTC TTTTCTTTCT GTTTCCTTTT     180

TTCCCCCTTG TTCCTTCTCC CTCTTCTTTG TAACTAACAA AACCACCACC AACTCCTCCT     240

CCTGCTGCTG CCCTTCCTCC TCCTCCTCAG TCCAAGTGAT CACAAAAGAA ATCTTCTGAG     300

CCGGAGGCGG TGGCATTTTT TAAAAAGCAA GCACATTGGA GAGAAAGAAA AAGAAAAACA     360

AAACCAAAAC AAAACCCAGG CACCAGACAG CCAGAACATT TTTTTTTCAC CCTTCCTGAA     420

AACAAACAAA CAAACAAACA ATCATCAAAA CAGTCACCAC CAACATCAAA ACTGTTAACA     480

TAGCGGCGGC GGCGGCAAAC GTCACCCTGC AGCCACGGCG TCCGCCTAAA GGGATGGTTT     540

TCTCGGCAGA GCAGCTCTTC GCCGACCACC TTCTTCACTC GTGCTGAGCG GGATTTTTGG     600

GCTCTCCGGG GTTCGGGCTG GGAGCAGCTT CATGACTACG CGGAGCGGGA GAGCGGCCAC     660

ACCATGCGAG CACAAATTGA AGTGATACCA TGCAAAATTT GTGGCGATAA GTCCTCTGGG     720

ATCCACTACG GAGTCATCAC ATGTGAAGGC TGCAAGGGAT TCTTTAGGAG GAGCCAGCAG     780

AACAATGCTT CTTATTCCTG CCCAAGGCAG AGAAACTGTT TAATTGACGG AACGAACAGA     840

AACCGTTGCC AACACTGCCG ACTGCAGAAG TGTCTTGCCC TAGGAATGTC AAGAGATGCT     900

GTGAAGTTTG GGAGAATGTC CAAGAAGCAA AGGGACAGCC TGTATGCTGA GGTGCAGAAG     960

CACCAGCAGC GGCTGCAGGA ACAGCGGCAG CAGCAGAGTG GGGAGGCAGA AGCCCTTGCC    1020

AGGGTGTACA GCAGCAGCAT TAGCAACGGC CTGAGCAACC TGAACAACGA GACCAGCGGC    1080

ACTTATGCCA ACGGGCACGT CATTGACCTG CCCAAGTCTG AGGGTTATTA CAACGTCGAT    1140

TCCGGTCAGC CGTCCCCTGA TCAGTCAGGA CTTGACATGA CTGGAATCAA ACAGATAAAG    1200

CAAGAACCTA TCTATGACCT CACATCCGTA CCCAACTTGT TTACCTATAG CTCTTTCAAC    1260

AATGGGCAGT TAGCACCAGG GATAACCATG ACTGAAATCG ACCGAATTGC ACAGAACATC    1320

ATTAAGTCCC ATTTGGAGAC ATGTCAATAC ACCATGGAAG AGCTGCACCA GCTGGCGTGG    1380

CAGACCCACA CCTATGAAGA AATTAAAGCA TATCAAAGCA AGGTACTCTG GAAACCATG    1440

AGAAAGTTTT TCTGTGATTA CCCTATTGCT GTGTTGCTCA AGCTCAGCAC TATTGGCATG    1500

TTGCACTGGG CAATTCTTTT CTGTAAGGGC ATCCTGCAAA TTGTTCGATA CTTACCAGCA    1560

TCCCTGGCCC TACCCACTAG ATGTGCCATC GCCCTCACAC ACACTTGTGA CAACCAGAAA    1620

TGTCTCCAGA TACTGCCAAC TGTTTCCAAG GAGGCAAAAC TACCCTGATT GAAAACCAC    1680

TGCCCTATTT GAGTGACTAC AGAGACCGTG CCTTCATCAA ATGATTTAG GACATCTCTT    1740

GCTGACTTCT TGGGTGGAGG CAAGGAGCAG GAGCAATGTA ATAATCACAG CAGTTGTAAT    1800

CGTCACAAAC TTACACAGCA AATATATGGA ACAAGGCTTT CTAAAGTTTT TCTTGCCCT    1860

GCATGTTAAA AAGAATCCAA AAAACAGGAC AACTCATCCC ATATTTTCAT TATTACACTG    1920

TGTCATTTCT TTGGGTTTGT TGAAGAAGTT TTTAAGAGGA ATTTATTGTT GTTTTTCAGT    1980

ATTTACATTA CATTACTTTG GGATAGAGAT CCCCAATTAC AAAATCCACC AGTAGATGGA    2040

ACTTTAATAA AATATATAAA TGTGACCTGC CCGGGCGGCC GCTCGAGCCC TATA          2094
```

(2) INFORMATION FOR SEQ ID NO:2:

(i) SEQUENCE CHARACTERISTICS:
        (A) LENGTH: 689 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Leu Thr Ile Gly Leu Glu Arg Pro Pro Gly Gln Val Ser Leu Ala Ala
1               5                   10                  15

Pro Phe Leu Pro Val Thr Glu Gln Lys Phe Thr Leu Trp Ile Arg Gln
            20                  25                  30

Ala Gln Met Ser Cys Glu Asn Ala His Ala Leu Pro Ser Thr Pro Pro
        35                  40                  45

Phe Phe Leu Phe Phe Leu Phe Pro Phe Phe Pro Leu Val Pro Ser Pro
    50                  55                  60

Ser Ser Leu Leu Thr Lys Pro Pro Thr Pro Pro Ala Ala Ala
65              70                  75                  80

Leu Pro Pro Pro Gln Ser Lys Ser Gln Lys Lys Ser Ser Glu Pro
                85                  90                  95

Glu Ala Val Ala Phe Phe Lys Lys Gln Ala His Trp Arg Glu Arg Lys
                100                 105                 110

Arg Lys Thr Lys Pro Lys Gln Asn Pro Gly Thr Arg Gln Pro Glu His
            115                 120                 125

Phe Phe Phe Thr Leu Pro Glu Asn Lys Gln Thr Asn Lys Gln Ser Ser
    130                 135                 140

Lys Gln Ser Pro Pro Thr Ser Lys Leu Leu Thr Arg Arg Arg Gln
145                 150                 155                 160

Thr Ser Pro Cys Ser His Gly Val Arg Leu Lys Gly Trp Phe Ser Arg
                165                 170                 175

Gln Ser Ser Ser Ser Pro Thr Thr Phe Phe Thr Arg Ala Glu Arg Asp
            180                 185                 190

Phe Trp Ala Leu Arg Gly Ser Gly Trp Glu Gln Leu His Asp Tyr Ala
        195                 200                 205

Glu Arg Glu Ser Gly His Thr Met Arg Ala Gln Ile Glu Val Ile Pro
    210                 215                 220

Cys Lys Ile Cys Gly Asp Lys Ser Ser Gly Ile His Tyr Gly Val Ile
225                 230                 235                 240

Thr Cys Glu Gly Cys Lys Gly Phe Phe Arg Arg Ser Gln Gln Asn Asn
                245                 250                 255

Ala Ser Tyr Ser Cys Pro Arg Gln Arg Asn Cys Leu Ile Asp Gly Thr
            260                 265                 270

Asn Arg Asn Arg Cys Gln His Cys Arg Leu Gln Lys Cys Leu Ala Leu
        275                 280                 285

Gly Met Ser Arg Asp Ala Val Lys Phe Gly Arg Met Ser Lys Lys Gln
    290                 295                 300

Arg Asp Ser Leu Tyr Ala Glu Val Gln Lys His Gln Gln Arg Leu Gln
305                 310                 315                 320

Glu Gln Arg Gln Gln Gln Ser Gly Glu Ala Glu Ala Leu Ala Arg Val
                325                 330                 335

Tyr Ser Ser Ile Ser Asn Gly Leu Ser Asn Leu Asn Asn Glu Thr
            340                 345                 350

Ser Gly Thr Tyr Ala Asn Gly His Val Ile Asp Leu Pro Lys Ser Glu
        355                 360                 365

Gly Tyr Tyr Asn Val Asp Ser Gly Gln Pro Ser Pro Asp Gln Ser Gly
    370                 375                 380

Leu Asp Met Thr Gly Ile Lys Gln Ile Lys Gln Glu Pro Ile Tyr Asp
385                 390                 395                 400
```

```
Leu Thr Ser Val Pro Asn Leu Phe Thr Tyr Ser Ser Phe Asn Asn Gly
                405                 410                 415

Gln Leu Ala Pro Gly Ile Thr Met Thr Glu Ile Asp Arg Ile Ala Gln
            420                 425                 430

Asn Ile Ile Lys Ser His Leu Glu Thr Cys Gln Tyr Thr Met Glu Glu
            435                 440                 445

Leu His Gln Leu Ala Trp Gln Thr His Thr Tyr Glu Glu Ile Lys Ala
    450                 455                 460

Tyr Gln Ser Lys Val Leu Trp Glu Thr Met Arg Lys Phe Phe Cys Asp
465                 470                 475                 480

Tyr Pro Ile Ala Val Leu Leu Lys Leu Ser Thr Ile Gly Met Leu His
            485                 490                 495

Trp Ala Ile Leu Phe Cys Lys Gly Ile Leu Gln Ile Val Arg Tyr Leu
            500                 505                 510

Pro Ala Ser Leu Ala Leu Pro Thr Arg Cys Ala Ile Ala Leu Thr His
            515                 520                 525

Thr Cys Asp Asn Gln Lys Cys Leu Gln Ile Leu Pro Thr Val Ser Lys
            530                 535                 540

Glu Ala Lys Leu Pro Leu Lys Asn His Cys Pro Ile Val Thr Thr Glu
545                 550                 555                 560

Thr Val Pro Ser Ser Asn Asp Phe Arg Thr Ser Leu Ala Asp Phe Leu
                565                 570                 575

Gly Gly Gly Lys Glu Gln Glu Gln Cys Asn Asn His Ser Ser Cys Asn
            580                 585                 590

Arg His Lys Leu Thr Gln Gln Ile Tyr Gly Thr Arg Leu Ser Lys Val
            595                 600                 605

Phe Ser Cys Pro Ala Cys Lys Glu Ser Lys Lys Gln Asp Asn Ser Ser
            610                 615                 620

His Ile Phe Ile Ile Thr Leu Cys His Phe Phe Gly Phe Val Glu Glu
625                 630                 635                 640

Val Phe Lys Arg Asn Leu Leu Leu Phe Phe Ser Ile Tyr Ile Thr Leu
            645                 650                 655

Leu Trp Asp Arg Asp Pro Gln Leu Gln Asn Pro Pro Val Asp Gly Thr
            660                 665                 670

Leu Ile Lys Tyr Ile Asn Val Thr Cys Pro Gly Gly Arg Ser Ser Pro
            675                 680                 685

Ile (2) INFORMATION FOR SEQ ID NO:3:

(i) SEQUENCE CHARACTERISTICS:
        (A) LENGTH: 556 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Asn Glu Gly Ala Pro Gly Asp Ser Asp Leu Glu Thr Glu Ala Arg
  1             5                  10                  15

Val Pro Trp Ser Ile Met Gly His Cys Leu Arg Thr Gly Gln Ala Arg
            20                  25                  30

Met Ser Ala Thr Pro Thr Pro Ala Gly Glu Gly Ala Arg Arg Asp Glu
            35                  40                  45

Leu Phe Gly Ile Leu Gln Ile Leu His Gln Cys Ile Leu Ser Ser Gly
```

```
            50                  55                  60
Asp Ala Phe Val Leu Thr Gly Val Cys Cys Ser Trp Arg Gln Asn Gly
 65                  70                  75                  80

Lys Pro Pro Tyr Ser Gln Lys Glu Asp Lys Glu Val Gln Thr Gly Tyr
                 85                  90                  95

Met Asn Ala Gln Ile Glu Ile Ile Pro Cys Lys Ile Cys Gly Asp Lys
                100                 105                 110

Ser Ser Gly Ile His Tyr Gly Val Ile Thr Cys Glu Gly Cys Lys Gly
            115                 120                 125

Phe Phe Arg Arg Ser Gln Gln Ser Asn Ala Thr Tyr Ser Cys Pro Arg
130                 135                 140

Gln Lys Asn Cys Leu Ile Asp Arg Thr Ser Arg Asn Arg Cys Gln His
145                 150                 155                 160

Cys Arg Leu Gln Lys Cys Leu Ala Val Gly Met Ser Arg Asp Ala Val
                165                 170                 175

Lys Phe Gly Arg Met Ser Lys Lys Gln Arg Asp Ser Leu Tyr Ala Glu
                180                 185                 190

Val Gln Lys His Arg Met Gln Gln Gln Arg Asp His Gln Gln Gln
            195                 200                 205

Pro Gly Glu Ala Glu Pro Leu Thr Pro Thr Tyr Asn Ile Ser Ala Asn
            210                 215                 220

Gly Leu Thr Glu Leu His Asp Asp Leu Ser Asn Tyr Ile Asp Gly His
225                 230                 235                 240

Thr Pro Glu Gly Ser Lys Ala Asp Ser Ala Val Ser Ser Phe Tyr Leu
                245                 250                 255

Asp Ile Gln Pro Ser Pro Asp Gln Ser Gly Leu Asp Ile Asn Gly Ile
                260                 265                 270

Lys Pro Glu Pro Ile Cys Asp Tyr Thr Pro Ala Ser Gly Phe Phe Pro
                275                 280                 285

Tyr Cys Ser Phe Thr Asn Gly Glu Thr Ser Pro Thr Val Ser Met Ala
                290                 295                 300

Glu Leu Glu His Leu Ala Gln Asn Ile Ser Lys Ser His Leu Glu Thr
305                 310                 315                 320

Cys Gln Tyr Leu Arg Glu Glu Leu Gln Gln Ile Thr Trp Gln Thr Phe
                325                 330                 335

Leu Gln Glu Glu Ile Glu Asn Tyr Gln Asn Lys Gln Arg Glu Val Met
                340                 345                 350

Trp Gln Leu Cys Ala Ile Lys Ile Thr Glu Ala Ile Gln Tyr Val Val
            355                 360                 365

Glu Phe Ala Lys Arg Ile Asp Gly Phe Met Glu Leu Cys Gln Asn Asp
            370                 375                 380

Gln Ile Val Leu Leu Lys Ala Gly Ser Leu Glu Val Val Phe Ile Arg
385                 390                 395                 400

Met Cys Arg Ala Phe Asp Ser Gln Asn Asn Thr Val Tyr Phe Asp Gly
                405                 410                 415

Lys Tyr Ala Ser Pro Asp Val Phe Lys Ser Leu Gly Cys Glu Asp Phe
                420                 425                 430

Ile Ser Phe Val Phe Glu Phe Gly Lys Ser Leu Cys Ser Met His Leu
                435                 440                 445

Thr Glu Asp Glu Ile Ala Leu Phe Ser Ala Phe Val Leu Met Ser Ala
                450                 455                 460

Asp Arg Ser Trp Leu Gln Glu Lys Val Lys Ile Glu Lys Leu Gln Gln
465                 470                 475                 480
```

```
Lys Ile Gln Leu Ala Leu Gln His Val Leu Gln Lys Asn His Arg Glu
            485                 490                 495

Asp Gly Ile Leu Thr Lys Leu Ile Cys Lys Val Ser Thr Leu Arg Ala
            500                 505                 510

Leu Cys Gly Arg His Thr Glu Lys Leu Met Ala Phe Lys Ala Ile Tyr
            515                 520                 525

Pro Asp Ile Val Arg Leu His Phe Pro Leu Tyr Lys Glu Leu Phe
            530                 535                 540

Thr Ser Glu Phe Glu Pro Ala Met Gln Ile Asp Gly
545                 550                 555

(2) INFORMATION FOR SEQ ID NO:4:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Asp Phe Trp Val Leu Trp Gly Ser Gly Trp Glu Leu His Asp Tyr
1               5                   10                  15

Thr Glu Gln Asp Ser Gly His Ile Met Arg Ala Gln Ile Glu Val Ile
            20                  25                  30

Pro Cys Lys Ile Cys Gly Asp Lys Ser Ser Gly Ile His Tyr Gly Val
            35                  40                  45

Ile Thr Cys Glu Gly Cys Lys Gly Phe Phe Arg Arg Ser Gln Gln Asn
50                  55                  60

Asn Ala Ser Tyr Ser Cys Pro Arg Gln Arg Asn Cys Leu Ile Asp Arg
65                  70                  75                  80

Thr Asn Arg Asn Arg Cys Gln His Cys Arg Leu Gln Lys Cys Leu Ala
            85                  90                  95

Leu Gly Met Ser Arg Asp Ala Val Lys Phe Gly Arg Met Ser Lys Lys
            100                 105                 110

Gln Arg Asp Ser Leu Tyr Ala Glu Val Gln Lys His Gln Gln Arg Leu
            115                 120                 125

Gln Glu Gln Arg Gln Gln Gln Ser Gly Glu Ala Glu Ala Leu Ala Arg
            130                 135                 140

Val Tyr Ser Ser Ser Ile Ser Asn Gly Leu Ser Asn Leu Asn Thr Glu
145                 150                 155                 160

Thr Gly Gly Thr Tyr Ala Asn Gly His Val Ile Asp Leu Pro Lys Ser
            165                 170                 175

Glu Gly Tyr Tyr Asn Ile Asp Ser Gly Gln Pro Ser Pro Asp Gln Ser
            180                 185                 190

Gly Leu Asp Met Thr Gly Ile Lys Gln Ile Lys Gln Glu Pro Ile Tyr
            195                 200                 205

Asp Leu Thr Ser Val His Asn Leu Phe Thr Tyr Ser Ser Phe Asn Asn
            210                 215                 220

Gly Gln Leu Ala Pro Gly Ile Thr Met Ser Glu Ile Asp Arg Ile Ala
225                 230                 235                 240

Gln Asn Ile Ile Lys Ser His Leu Glu Thr Cys Gln Tyr Thr Met Glu
            245                 250                 255

Glu Leu His Gln Leu Ala Trp Gln Thr His Thr Tyr Glu Glu Ile Lys
            260                 265                 270
```

```
Ala Tyr Gln Ser Lys Ser Arg Glu Ala Leu Trp Gln Gln Cys Ala Ile
        275                 280                 285
Gln Ile Thr His Ala Ile Gln Tyr Val Val Glu Phe Ala Lys Arg Ile
        290                 295                 300
Thr Gly Phe Met Glu Leu Cys Gln Asn Asp Gln Ile Leu Leu Leu Lys
305                 310                 315                 320
Ser Gly Cys Leu Glu Val Leu Val Arg Met Cys Arg Ala Phe Asn
                325                 330                 335
Pro Leu Asn Asn Thr Val Leu Phe Glu Gly Lys Tyr Gly Gly Met Gln
            340                 345                 350
Met Phe Lys Ala Leu Gly Ser Asp Asp Leu Val Asn Glu Ala Phe Asp
            355                 360                 365
Phe Ala Lys Asn Leu Cys Ser Leu Gln Leu Thr Glu Glu Ile Ala
        370                 375                 380
Leu Phe Ser Ser Ala Val Leu Ile Ser Pro Asp Arg Ala Trp Leu Leu
385                 390                 395                 400
Glu Pro Arg Lys Val Gln Lys Leu Gln Glu Lys Ile Tyr Phe Ala Leu
            405                 410                 415
Gln His Val Ile Gln Lys Asn His Leu Asp Asp Glu Thr Leu Ala Lys
            420                 425                 430
Leu Ile Ala Lys Ile Pro Thr Ile Thr Ala Val Cys Asn Leu His Gly
        435                 440                 445
Glu Lys Leu Gln Val Phe Lys Gln Ser His Pro Asp Ile Val Asn Thr
        450                 455                 460
Leu Phe Pro Pro Leu Tyr Lys Glu Leu Phe Asn Pro Asp Cys Ala Ala
465                 470                 475                 480
Val Cys Lys (2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC10442

(xi) SEQUENCE DESCRIPTION: SEQ ID NO:5:

CTGTTCGTTC TGTCAATTAA AAAGT                                      25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC10443

(xi) SEQUENCE DESCRIPTION: SEQ ID NO:6:

CCACCAACAT CAAAACTGTT AACAT                                      25
```

```
(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC10558

(xi) SEQUENCE DESCRIPTION: SEQ ID NO:7:

TCCGTAGTGG ATCCCAGAGG ACTTATC                                              27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC10559

(xi) SEQUENCE DESCRIPTION: SEQ ID NO:8:

CCCAGAGGAC TTATCGCCAC AAATTTT                                              27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC10555

(xi) SEQUENCE DESCRIPTION: SEQ ID NO:9:

TCGGGCTGGG AGCAGCTTCA TGACTAC                                              27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC10556

(xi) SEQUENCE DESCRIPTION: SEQ ID NO:10:

CAGCTTCATG ACTACGCGGA GCGGGAG                                              27

(2) INFORMATION FOR SEQ ID NO:11:

(i) SEQUENCE CHARACTERISTICS:
        (A) LENGTH: 2067 base pairs
        (B) TYPE: nucleic acid
        (C) STRANDEDNESS: single
        (D) TOPOLOGY: linear
```

-continued

```
(xi) SEQUENCE DESCRIPTION: SEQ ID NO:11:

YTNACNATHG GNYTNGARMG NCCNCCNGGN CARGTNWSNY TNGCNGCNCC NTTYYTNCCN     60

GTNACNGARC ARAARTTYAC NYTNTGGATH MGNCARGCNC ARATGWSNTG YGARAAYGCN    120

CAYGCNYTNC CNWSNACNCC NCCNTTYTTY YTNTTYTTYY TNTTYCCNTT YTTYCCNYTN    180

GTNCCNWSNC CNWSNWSNYT NYTNACNAAR CCNCCNCCNA CNCCNCCNCC NGCNGCNGCN    240

YTNCCNCCNC CNCCNCARWS NAARWSNCAR AARAARWSNW SNGARCCNGA RGCNGTNGCN    300

TTYTTYAARA ARCARGCNCA YTGGMGNGAR MGNAARMGNA ARACNAARCC NAARCARAAY    360

CCNGGNACNM GNCARCCNGA RCAYTTYTTY TTYACNYTNC CNGARAAYAA RCARACNAAY    420

AARCARWSNW SNAARCARWS NCCNCCNACN WSNAARYTNY TNACNMGNMG NMGNMGNCAR    480

ACNWSNCCNT GYWSNCAYGG NGTNMGNYTN AARGGNTGGT TYWSNMGNCA RWSNWSNWSN    540

WSNCCNACNA CNTTYTTYAC NMGNGCNGAR MGNGAYTTYT GGGCNYTNMG NGGNWSNGGN    600

TGGGARCARY TNCAYGAYTA YGCNGARMGN GARWSNGGNC AYACNATGMG NGCNCARATH    660

GARGTNATHC CNTGYAARAT HTGYGGNGAY AARWSNWSNG GNATHCAYTA YGGNGTNATH    720

ACNTGYGARG GNTGYAARGG NTTYTTYMGN MGNWSNCARC ARAAYAAYGC NWSNTAYWSN    780

TGYCCNMGNC ARMGNAAYTG YYTNATHGAY GGNACNAAYM GNAAYMGNTG YCARCAYTGY    840

MGNYTNCARA ARTGYYTNGC NYTNGGNATG WSNMGNGAYG CNGTNAARTT YGGNMGNATG    900

WSNAARAARC ARMGNGAYWS NYTNTAYGCN GARGTNCARA ARCAYCARCA RMGNYTNCAR    960

GARCARMGNC ARCARCARWS NGGNGARGCN GARGCNYTNG CNMGNGTNTA YWSNWSNWSN   1020

ATHWSNAAYG GNYTNWSNAA YYTNAAYAAY GARACNWSNG GNACNTAYGC NAAYGGNCAY   1080

GTNATHGAYY TNCCNAARWS NGARGGNTAY TAYAAYGTNG AYWSNGGNCA RCCNWSNCCN   1140

GAYCARWSNG GNYTNGAYAT GACNGGNATH AARCARATHA ARCARGARCC NATHTAYGAY   1200

YTNACNWSNG TNCCNAAYYT NTTYACNTAY WSNWSNTTYA AYAAYGGNCA RYTNGCNCCN   1260

GGNATHACNA TGACNGARAT HGAYMGNATH GCNCARAAYA THATHAARWS NCAYYTNGAR   1320

ACNTGYCART AYACNATGGA RGARYTNCAY CARYTNGCNT GGCARACNCA YACNTAYGAR   1380

GARATHAARG CNTAYCARWS NAARGTNYTN TGGGARACNA TGMGNAARTT YTTYTGYGAY   1440

TAYCCNATHG CNGTNYTNYT NAARYTNWSN ACNATHGGNA TGYTNCAYTG GGCNATHYTN   1500

TTYTGYAARG GNATHYTNCA RATHGTNMGN TAYYTNCCNG CNWSNYTNGC NYTNCCNACN   1560

MGNTGYGCNA THGCNYTNAC NCAYACNTGY GAYAAYCARA ARTGYYTNCA RATHYTNCCN   1620

ACNGTNWSNA ARGARGCNAA RYTNCCNYTN AARAAYCAYT GYCCNATHGT NACNACNGAR   1680

ACNGTNCCNW SNWSNAAYGA YTTYMGNACN WSNYTNGCNG AYTTYYTNGG NGGNGGNAAR   1740

GARCARGARC ARTGYAAYAA YCAYWSNWSN TGYAAYMGNC AYAARYTNAC NCARCARATH   1800

TAYGGNACNM GNYTNWSNAA RGTNTTYWSN TGYCCNGCNT GYAARGARWS NAARAARCAR   1860

GAYAAYWSNW SNCAYATHTT YATHATHACN YTNTGYCAYT TYTTYGGNTT YGTNGARGAR   1920

GTNTTYAARM GNAAYYTNYT NYTNTTYTTY WSNATHTAYA THACNYTNYT NTGGGAYMGN   1980

GAYCCNCARY TNCARAAYCC NCCNGTNGAY GGNACNYTNA THAARTAYAT HAAYGTNACN   2040

TGYCCNGGNG GNMGNWSNWS NCCNATH                                       2067
```

NUCLEAR RECEPTOR POLYPEPTIDE ZPPAR4

REFERENCE TO RELATED APPLICATION

This application is related to Provisional Application No. 60/051,032, filed on Jun. 27, 1997. Under 35 U.S.C. §119 (e)(1), this application claims benefit of said Provisional Application.

BACKGROUND OF THE INVENTION

Non-peptide hormones are involved in coordination of multiple events related to development, differentiation and physiological response to a wide range of stimuli. These hormones bind to intracellular nuclear hormone receptors that mediate the hormonal effect. Nuclear hormone receptors (NHRs) have been identified as ligand-dependent transcription factors that initiate nuclear responses to steroids, retinoids, 1,25 dihydroxyvitamin $D_3$ and thyroid hormones. Peroxisome proliferator-activated receptors (PPARs) are also members of the NHR family. Based on shared characteristics, a superfamily of nuclear hormone receptors has been recognized. The superfamily also includes structurally related proteins for which no ligand has been identified ("orphan receptors").

Members of the NHR superfamily share structural similarity. The majority exhibit three prinicipal domains: (1) a variable, amino-terminal domain that often is related to transactivating activity; (2) a highly conserved DNA binding domain; and (3) a moderately conserved carboxy-terminal ligand-binding domain. The DNA binding domain has two "zinc finger" motifs, and differences in the sequence of these motifs have been associated with differences in DNA binding or receptor dimerization or its absence. Further, the region immediately carboxy-terminal of the zinc fingers has been implicated in DNA recognition. This region contains two adjacent clusters of amino acids referred to as the "A- and T-boxes." Differences in these regions correlate with the subdivision of the superfamily into four groups: (I) receptors that act as homodimers; (II) receptors that act as both homodimers and heterodimers; (III) receptors that act as monomers; and (IV) receptors that bind exclusively as heterodimers.

NHRs (also termed "nuclear receptors") bind to DNA sequences, called "response elements", in the promoter region of target genes. These response elements have distinct sequence motifs, and the relative orientation and spacing of these sequence motifs are important for receptor binding specificity.

One family of NHRs, the retinoid-related receptors, has been subdivided into a number of classes, including RAR (retinoic acid receptors), RXR (retinoid X receptors), RZR (retinoid Z receptors) and ROR (RAR-related orphan receptors). RZRs were reported to bind to natural retinoid response elements (hexameric (A/G)GGTCA core half-site motif) as monomers (C. Carlberg et al., *Mol. Endocrinol.* 8:757–70, 1994). In addition, RZRs preferred a T at the −1 position to the core motif; at position −2, all nucleotides were comparable in binding efficiency. RZR receptor transactivation activity closely paralleled DNA binding efficiency. When the two core motif half-sites were present in certain configurations tested, RZRs could bind cooperatively as homodimers. Further, transactivation by RZRs appeared to be constitutive.

The Rev-erba and Rev-erbp orphan nuclear receptors are highly related to each other and to the (ROR)/RZR subfamily of receptors (B. M. Forman et al., *Molec. Endocrinol.* 8:1253–61, 1994). The Rev-erb receptors bind as monomers to a Rev-erb/RORα1 common response element sequence, AATGT-AGGTCA. However, while RORα1 constitutively activates transcription through this sequence, both Rev-erb isoforms are inactive. When coexpressed with RORα1, the Rev-erb isoforms suppress the transcriptional activity of RORα1.

The natural ligands for certain members of the nuclear hormone receptor family have been identified recently. For instance, 9-cis retinoic acid has been identified as the natural ligand for the RXR orphan receptor family (A. A. Levin et al., *Nature* 355:359–61, 1992; R. A. Heyman et al., *Cell* 68:397–406, 1992).

Melatonin has been identified as the natural ligand for RZRβ receptors (M. Becker-Andre et al., *J. Biol. Chem.* 269:28531–34, 1994). In the central nervous system, RZRβ mRNA is most prominent in pineal gland, thalamus and hypothalamus, while in the periphery only the adrenal gland was reported as positive. A more detailed examination localized RZRβ mRNA in the neural retina, the suprachiasmatic nucleau and the superficial gray layer of the superior colliculus. This tissue distribution is consistent with the distribution of binding sites for melatonin. In cells transfected with RZRβ, fetal calf serum (FCS) increased basal constitutive activity of RZRβ. This activation was ameliorated when FCS was treated with charcoal or anti-melatonin antibody plus protein A-Sepharose. A component of FCS was speculated to be involved in post-translational modification of RZRβ (i.e., perhaps phosphorylation by protein kinases).

Subsequently, melatonin was reported to bind to RZRα and its splice variant RORα1 (I. Wiesenberg et al., *Nucl. Acids Res.* 23:327–33, 1995). In contrast to RZRβ, RZRα/RORα1 receptors are expressed in many tissues outside the brain. A synthetic RZR ligand, thiazolidinedione CGP 52608, also binds to RZRα/RORα1. However, this synthetic ligand does not bind to the high affinity membrane receptor for melatonin. Further, a class of thiazolidinediones exhibited anti-arthritic effects in vivo that correlated with RZR/RORα activation (M. Missbach et al., *J. Biol. Chem.* 271:13515–22, 1996).

Thiazolidinediones have also been described as high affinity ligands for PPARγ, which functions in adipogenesis (J. M. Lehmann et al., *J. Biol. Chem.* 270:12953–56, 1995). Thiazolidinedione derivatives are anti-diabetic agents that act as insulin sensitizers. A prostaglandin $J_2$ ($PGJ_2$) metabolite, 15-deoxy-$\Delta^{12,14}$-$PGJ_2$, binds to PPARγ also, and promoted differentiation of fibroblasts to adipocytes (S. A. Kliewer et al., *Cell* 83:813–19, 1996).

Recently, 5-lipoxygenase has been reported to be an RZR/melatonin responding gene (D. Steinhilber et al., *J. Biol. Chem.* 270:7037–40, 1995). This enzyme is not found in the brain, but instead acts in the periphery, particularly in myeloid cells.

Another ROR/RZR receptor, RORγ, has been reported to be highly expressed in skeletal tissue (T. Hirose et al., *Biochem. Biophys. Res. Comm.* 205:1976–83, 1994). The amino acid sequence of RORγ was 50% and 51% identical to those of RORα/RZRα and RZRβ, respectively, with DNA binding domains having 89% identity.

Because orphan nuclear receptors generally regulate important biological processes, identification of novel orphan nuclear receptors furthers an understanding of the complex transcriptional networks in which such receptors function. Identification and characterization of new orphan receptors permits further dissection of the activities of related receptors. A novel orphan receptor provides a means to find the natural ligand for that receptor. By identifying the corresponding ligand, the physiological role of the orphan receptor can be determined.

The present invention provides a novel orphan nuclear receptor for these and other uses that should be apparent to those skilled in the art from the teachings herein.

SUMMARY OF THE INVENTION

The present invention provides a novel human nuclear hormone receptor polypeptide and related compositions and methods.

Within one aspect there is provided an isolated polynucleotide molecule encoding a ZPPAR4 nuclear receptor polypeptide that is at least 80% identical to an amino acid sequence of SEQ ID NO:2 from amino acid residue 222 (Met) to amino acid residue 680 (Ile). Within another embodiment is provided an isolated polynucleotide molecule encoding a ZPPAR4 nuclear receptor polypeptide selected from the group consisting of: a) a polypeptide comprising an amino acid sequence as shown in SEQ ID NO:2 from amino acid residue 222 (Met) to amino acid residue 475 (Val); and b) species orthologs of (a). Within yet another embodiment, the isolated polynucleotide molecule encodes a full-length human ZPPAR4 receptor polypeptide.

Within a second aspect of the invention there is provided an expression vector comprising a transcription promoter; a DNA segment encoding a ZPPAR4 nuclear receptor polypeptide that is at least 80% identical to an amino acid sequence of SEQ ID NO:2 from amino acid residue 222 (Met) to amino acid residue 680 (Ile); and a transcription terminator. Within another embodiment is provided a cultured cell into which has been introduced an expression vector which expresses the ZPPAR4 nuclear receptor polypeptide encoded by the DNA segment.

Within a third aspect of the invention is provided an isolated ZPPAR4 receptor polypeptide, wherein the isolated ZPPAR4 receptor polypeptide is selected from the group consisting of: a) a polypeptide comprising an amino acid sequence as shown in SEQ ID NO:2 from amino acid residue 222 (Met) to amino acid residue 475 (Val); b) an allelic variant of (a); and c) a species ortholog of (a) or (b). Within another embodiment, an isolated ZPPAR4 receptor polypeptide is at least 80% identical to an amino acid sequence as shown in SEQ ID NO:2 from amino acid residue 222 (Met) to amino acid residue 680 (Ile).

Within a fourth aspect of the invention is provided a method for producing a ZPPAR4 nuclear receptor polypeptide comprising the steps of culturing a cell into which has been introduced an expression vector, whereby the cell expresses a ZPPAR4 nuclear receptor polypeptide encoded by the DNA segment; and recovering the ZPPAR4 nuclear receptor polypeptide.

The invention further provides an isolated antibody that binds to an epitope of a polypeptide as disclosed above.

The invention also provides a method for modulating ZPPAR4-mediated transcription of a target gene in a cell, comprising the steps of incubating a test compound with eukaryotic cells that express ZPPAR4 nuclear receptor polypeptide; and measuring the ZPPAR4-mediated transcription of the target gene in the presence and in the absence of the test compound, or measuring the effect of the test compound on target gene transcription in ZPPAR4-overexpressing (+) cells and in ZPPAR4-deficient (−) cells, whereby a difference in target gene transcription in the presence and absence of test compound, or in ZPPAR4-overexpressing (+) cells and in ZPPAR4-deficient (−) cells, indicates a test compound that modulates ZPPAR4-mediated transcription of the target gene.

These and other aspects of the invention will become evident upon reference to the following detailed description and the attached drawings.

BRIEF DESCRIPTION OF THE DRAWING

The FIGURE illustrates a multiple alignment of amino acid sequences of ZPPAR4 (SEQ ID NO:2), rat RZRβ (SEQ ID NO:4), and human RORα2 (SEQ ID NO:3).

DETAILED DESCRIPTION OF THE INVENTION

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The terms "nuclear hormone receptor", "nuclear receptor" and "NHR" denote a ligand-dependent transcription factor that initiates nuclear responses to non-peptide hormones, such as steroids, retinoids, 1,25 dihydroxyvitamin $D_3$ and thyroid hormones.

The term "orphan receptor" denotes a receptor for which a corresponding ligand has not been identified.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). When applied to a protein, the term "isolated" indicates that the protein is found in a condition other than its native environment, such as apart from blood and animal tissue. In a preferred form, the isolated protein is substantially free of other proteins, particularly other protein of animal origin. It is preferred to provide the proteins in a highly purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complement of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The present invention is based in part upon the discovery of a novel human polynucleotide sequence (SEQ ID NO:1) that encodes a polypeptide (SEQ ID NO:2) having the structure of an RZR/ROR nuclear receptor. This novel polynucleotide and the polypeptide it encodes are designated "ZPPAR4". Analysis of the tissue distribution of the mRNA corresponding to this novel polynucleotide showed that expression was highest in skeletal muscle, heart and pancreas.

Those skilled in the art will readily recognize that, in view of the degeneracy of the genetic code, considerable sequence variation is possible among these polynucleotide molecules. SEQ ID NO:11 is a degenerate DNA sequence that encompasses all DNAs that encode the ZPPAR4 polypeptide of SEQ ID NO:2. Those skilled in the art will recognize that the degenerate sequence of SEQ ID NO:11 also provides all RNA sequences encoding SEQ ID NO:2 by substituting U for T. Thus, ZPPAR4 polypeptide-encoding degenerate DNA sequences of SEQ ID NO:11 and their RNA equivalents are contemplated by the present invention. Table 1 sets forth the one-letter codes used within SEQ ID NO:11 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |

TABLE 1-continued

| Nucleotide | Resolution | Nucleotide | Complement |
|---|---|---|---|
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:11, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

The FIGURE presents a multiple alignment of deduced amino acid sequences of ZPPAR4 (SEQ ID NO:2), human RORα2 (SEQ ID NO:3), and rat RZRβ (SEQ ID NO:4). As reported by Carlberg et al. in Mol. Endocrinol. 8:757–70, 1994, the RZRβ cDNA sequence extended about 400 nucleotides 5' of the first zinc finger motif; encoded methionine and stop codons in all three reading frames; and was believed to be part of a fully processed transcript. Because RZRβ and RZRα shared a methionine located 5' of the first zinc finger region, Carlberg et al. suggested that this residue was the initiation methionine. This shared RZRβ/RZRα methionine corresponds to Met 97 of SEQ ID NO:3 and Met 25 of SEQ ID NO:4. The N-terminal region of the deduced amino acid sequence of human RORα2 contains 4 methionine residues, corresponding to positions 1, 22, 33 and 97 of SEQ ID NO:3. Based on homology to the shared RZRβ/RZRα methionine, the initiation Met codon of human RORα2 may be the fourth Met residue (i.e., Met 97 of human RORα2, as shown in SEQ ID NO:3). Based on these homologies, amino acid residue Met 216 of SEQ ID NO:2 may be the natural initiation Met residue for ZPPAR4. Alternatively (or in addition), the Met 35 residue upstream of Met 216 may serve as a start site(s) for the encoded ZPPAR4 polypeptide. However, a stop codon appears to be present just prior to amino acid residue 156 of SEQ ID NO:2.

The reference rat RZRβ amino acid sequence is truncated in the N-terminal portion relative to the ZPPAR4 and human RORα2 amino acid sequences, and the human RORα2 amino acid sequence is truncated relative to the ZPPAR4 sequence. Within the N-terminal region of SEQ ID NO:2 (upstream of Met 216), the homology between ZPPAR4 and human RORα2 is not as striking as it is after Met 216. The ZPPAR4 deduced amino acid sequence shows striking homology to rat RZRβ and human RORα2 between positions Met 216 and Val 469 of SEQ ID NO:2 (encompassing a DNA binding domain, T-box, A-box and about 160 downstream residues).

By alignment with rat RZRβ and human RORα2 sequences, the encoded ZPPAR4 sequence contains a complete nuclear receptor domain organization. The novel ZPPAR4 polypeptide encoded by the polynucleotide described herein includes the DNA binding/zinc finger motif present in all members of the nuclear receptor superfamily. The two zinc finger motifs are highly conserved, wherein four cysteines in each finger coordinately bind a zinc atom within the finger. A consensus amino acid sequence of the DNA binding domain has been reported by M. Becker-Andre et al. (*Biochem. Biophys. Res. Comm.* 194:1371–79, 1993). This domain includes at least 66 amino acid residues, and about 20 invariant amino acid residues, including nine cysteines. The DNA binding domain of ZPPAR4 similarly contains 9 Cys residues.

When RZRα and RZRβ receptors are compared, the most conserved sequences are in the DNA binding domain (92% identity in amino acid residues); the putative ligand binding domain shows 62% identity (C. Carlberg et al., *Molec. Endocrinol.* 8:757–70, 1994). RZRβ receptors and Drosophila receptor DHR3 share 78% identity in the DNA binding domain, and 35r identity in their ligand binding domain. RZR receptor DNA binding domains also resemble those of RARs and RXRs [RARα (RZRα, 70%; RZRβ, 67%) and RXRα (65% and 62o, respectively)].

The highly conserved amino acids in the DNA binding domain of nuclear receptors can be used as a tool to identify new superfamily members. For instance, reverse transcription-polymerase chain reaction (RT-PCR) can be used to amplify sequences encoding the conserved DNA binding motif from RNA obtained from a variety of 4Th3 tissue sources. In particular, highly degenerate primers designed from the zinc finger sequences are useful for this purpose.

The novel RZR/ROR-encoding polynucleotides and RZR/ROR polypeptides of the present invention were initially identified by querying an EST database for sequences homologous to individual members of the nuclear receptor superfamily, as well as to conserved motifs within the family. Three EST sequences were discovered and were determined to be related to the rat RZRβ and human RORα4 family. A first EST (a second EST was subsumed within this first EST) corresponded to the N-terminal 82 amino acids of rat RZRβ; the third EST corresponded to the 3' end of a clone that contained one of the two N-terminal ESTs. Based on the EST sequence, oligonucleotide primers were selected and used in conjunction with a human fetal brain cDNA library, PCR and RACE to generate and sequence a full-length clone.

Within preferred embodiments of the invention, isolated ZPPAR4 polynucleotides will hybridize to similar-sized regions of SEQ ID NO:1, or a sequence complementary thereto, under stringent conditions. In general, stringent conditions are selected to be about 5° C. lower than the thermal melting point $(T_m)$ for the specific sequence at a defined ionic strength and pH. The Tm is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C. As previously noted, the isolated polynucleotides of the present invention include DNA and RNA. Methods for isolating DNA and RNA are well known in the art. It is generally preferred to isolate RNA from human fetal brain, skeletal muscle, heart or pancreas, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–12, 1972). Complementary DNA (cDNA) is prepared from poly$(A)^+$ RNA using known methods. Polynucleotides encoding ZPPAR4 polypeptides are then identified and isolated by, for example, hybridization or PCR.

The present invention further provides counterpart polypeptides and polynucleotides from other species (orthologs or paralogs). Of particular interest are ZPPAR4 polypeptides from other mammalian species, including murine, rat, porcine, ovine, bovine, canine, feline, equine and other primate proteins. Homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A ZPPAR4-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to ZPPAR4. Similar techniques can also be applied to the isolation of genomic clones.

Those skilled in the art will recognize that the sequences disclosed in SEQ ID NO:1 and SEQ ID NO:2 represent a single allele of the human ZPPAR4 polynucleotide and human ZPPAR4 polypeptide, respectively, and that allelic variation and alternative splicing are expected to occur. Allelic variants can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of the ZPPAR4 protein encoded by SEQ ID NO:1. Splice variants of nuclear receptors are also known. Therefore, splice variants, and particularly N-terminal splice variants, of ZPPAR4 may be expected to occur.

The present invention also provides isolated ZPPAR4 polypeptides that are substantially homologous to the polypeptide of SEQ ID NO:2 and its orthologs or paralogs. The term "substantially homologous" is used herein to denote polypeptides having 50%, preferably 60%, more preferably at least 80%, sequence identity to the sequence shown in SEQ ID NO:2 or its species homologs. Such polypeptides will more preferably be at least 90% identical, and most preferably 95% or more identical to SEQ ID NO:2 or its orthologs or paralogs. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes).

The percent identity is then calculated as:

$$\frac{\text{Total number of identical matches}}{[\text{length of the longer sequence plus the number of gaps introduced into the longer sequence in order to align the two sequences}]} \times 100$$

small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Meth. Enzymol.* 198:3, 1991), glutathione-S-transferase (Smith and Johnson, *Gene* 67:31, 1988), maltose binding protein (Kellerman and Ferenci, *Meth. Enzymol.* 90:459–63, 1982; Guan et al., *Gene* 67:21–30, 1987), thioredoxin, ubiquitin, cellulose binding protein, T7 polymerase, or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, everly, Mass.).

TABLE 4

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a TABLE 4-continued

| Conservative amino acid substitutions | |
|---|---|
| Small: | glycine |
|  | alanine |
|  | serine |
|  | threonine |
|  | methionine |

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of ZPPAR4. A limited number of non-conservative amino acids, amino acids that are not encoded by the genetic code, and unnatural amino acids may be substituted for ZPPAR4 amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the ZPPAR4 polypeptides of the present invention can be identified according to procedures known in the art, such as site-directed mutagenesis or alanine-scanning mutagenesis (Cunningham and Wells, *Science* 244: 1081–85, 1989). In the latter technique, single alanine mutations are introduced at every residue in the molecule, and the resultant mutant molecules are tested for biological activity (e.g., transcription or binding activity) to identify amino acid residues that are critical to the activity of the molecule. See also, Hilton et al., *J. Biol. Chem.* 271:4699–4708, 1996. Sites of ligand-receptor interaction and DNA-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related nuclear receptors.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–56, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–37, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides (e.g., transcription or DNA binding activity) can be recovered from the host cells and rapidly sequenced using modern equipment. These methods allow the rapid determination of the importance of individual amino acid residues in a polypeptide of interest, and can be applied to polypeptides of unknown structure. Using the methods discussed above, one of ordinary skill in the art can identify and/or prepare a variety of polypeptides that are substantially homologous to residues 2 to 689 of SEQ ID NO:2, and particularly to residues 216 to 674 of SEQ ID NO:2, or allelic variants thereof and that retain the transcription factor properties of the wild-type protein.

Key amino acid residues within the native ZPPAR4 polypeptide may also be determined by X-ray crystallography. For instance, the three-dimensional structure of the ligand-binding domain of ZPPAR4 polypeptide can be solved using X-ray crystallography. This approach has been used to describe the crystal structure of the ligand-binding domain of human RXR-α (W. Bourguet et al., *Nature* 375:377–82, 1995). For ZPPAR4, the resultant three-dimensional coordinates are informative starting points for the structure-based design of ZPPAR4-binding ligands, agonists and/or antagonists. More specifically and as an example, given the three-dimensional coordinates of the ZPPAR4 ligand binding site, along with a data set consisting of ZPPAR4 activity modulators, a negative image mold, suitable to accommodate the 3-D shape of potential ligands and to interact with their functional groups, can be obtained. This negative image mold is in essence a representation of the ligand binding site of ZPPAR4 polypeptide. Thus, molecules that would form strong bonding interactions with those amino acids identified as crucial for ligand binding can be designed.

The ZPPAR4 polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al. (eds.), *Current Protocols in Molecular Biology,* John Wiley and Sons, Inc., NY, 1987, which are incorporated herein by reference.

In general, a DNA sequence encoding a ZPPAR4 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a ZPPAR4 polypeptide into the secretory pathway of a host cell, a secretory signal sequence (also known as a leader sequence, prepro sequence or pre sequence) is provided in the expression vector. The secretory signal sequence may be that of the ZPPAR4 polypeptide, or may be derived from another secreted protein (e.g., t-PA) or synthesized de novo. The secretory signal sequence is joined to the ZPPAR4 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–45, 1982), DEAE-dextran mediated transfection (Ausubel et al., eds., *Current Protocols in Molecular Biology,* John Wiley and Sons, Inc., NY, 1987), liposome-mediated transfection (Hawley-Nelson et al., *Focus* 15:73, 1993; Ciccarone et al., *Focus* 15:80, 1993), and viral vectors (A. Miller and G. Rosman, *Bio-Techniques* 7:980–90, 1989; Q. Wang and M. Finer, *Nature Med.* 2:714–16, 1996), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of Agrobacterium rhizogenes as a vector for expressing genes in plant cells has been reviewed by Sinkar et al., *J. Biosci. (Bangalore)* 11:47–58, 1987.

Fungal cells, including yeast cells, and particularly cells of the genus Saccharomyces, can also be used within the present invention, such as for producing ZPPAR4 fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–65, 1986; and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Expressed recombinant ZPPAR4 polypeptides (or chimeric ZPPAR4 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988. A fusion of the polypeptide of interest and an affinity tag (e.g., polyhistidine, maltose-binding protein, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9i pure with respect to contaminating macromolecules, particularly other proteins and nucleic acids, and free of infectious and pyrogenic agents. Preferably, a purified protein is substantially free of other protein, particularly other protein of animal origin.

ZPPAR4 polypeptides or fragments thereof may also be prepared through chemical synthesis. ZPPAR4 polypeptides may be monomers or multimers; glycosylated or non-glycosylated; pegylated or non-pegylated; and may or may not include an initial methionine amino acid residue.

One or more small probes based on the sequences disclosed herein may be used to detect molecules encoding ZPPAR4 or related nuclear receptors. Of particular utility are labeled probes comprising an oligonucleotide of at least about 14 or more nucleotides and up to 25 or more nucleotides in length that are at least 80% identical to a same-length portion of SEQ ID NO: 1 or its complementary sequences. A library is then probed with such labeled oligonucleotide probe, preferably at a low hybridization stringency, i.e., about 2×SSC and a hybridization temperature of about 50° C. Molecules to which the labeled probe hybridizes are detected using standard label detection procedures. In addition, such oligonucleotide probes may be used for chromosomal identification and mapping.

Chimeric ZPPAR4 polypeptides can be designed and inserted into expression vectors, expressed by cultured host cells and used in an assay to screen for the natural ligand, as well as for agonists and antagonists of the natural ligand. Briefly, a polynucleotide sequence encoding the DNA binding domain of human ZPPAR4 is exchanged with a polynucleotide sequence encoding the DNA binding domain of a known human nuclear hormone receptor. Known, characterized nuclear hormone receptors, such as the estrogen and the glucocorticoid receptors, have been used successfully to create chimeric receptors for ligand determination (Giguere et al., *Nature* 330:624–29, 1987; Green and Chambon, *Nature* 325:75–78, 1987; Petkovich et al., *Nature* 330:444–50, 1987; and Issemann and Green, *Nature* 347:645–50, 1990). The chimeric receptor is then transfected into a host cell line that is deficient for the known NHR and has been engineered to express a reporter gene. Suitable reporter genes include the bacterial chloramphenicol acetyl transferase (CAT) coding sequence or a luciferase gene (de Wet et al., *Mol. Cell. Biol.* 7:725, 1987). The reporter gene is linked to a hormone response element (native or synthetic) that is responsive to the DNA binding domain of the known NHR used in the chimeric receptor. In some instances, the response element may be optimized and/or may be fused to a thymidine kinase (tk) promoter. The transfected host cell containing the chimeric receptor is exposed to a test sample. If the test sample contains at least one ligand that binds to the ligand-binding domain of ZPPAR4, the reporter gene is induced (or its expression is increased over a control, baseline level). For example, induction/expression of a luciferase reporter gene is detected by luminescence using methods known in the art (e.g., Baumgartner et al., *J. Biol. Chem.* 269:29094–101, 1994; Schenborn and Goiffin, *Promega Notes* 41:11, 1993). Luciferase activity assay kits are commercially available from, for example, Promega Corp., Madison, Wis. Chimeric receptor-containing cell lines of this type can be used to screen samples and/or libraries of chemicals, cell-conditioned culture media, biological fluids, fungal broths, soil samples, water samples, extracts of microorganisms, and the like.

Compounds identified as ZPPAR4 agonists and antagonists would be useful as therapeutic agents for modulating transcription of target genes. Agonist compounds could be used to influence cellular differentiation, proliferation or development through up-regulation of ZPPAR4-modulated gene expression. Antagonists can be used to out-compete endogenous, natural ZPPAR4 ligand, and to exert control over the receptor. Agonists and antagonists are also useful as research reagents for characterizing sites of ligand-receptor interaction. Agonists and antagonists may also prove useful in the study of modulation of biological processes. The ZPPAR4 polypeptides or fragments thereof may also act as antagonists to other nuclear hormone receptors mediating transcriptional activity.

The variety of transcription factors within a cell compete for transcriptional co-activators. A nuclear receptor/transcription factor binds to its appropriate recognition sequence, and then interacts with proteins ("co-activators") that enable up-regulation of target gene expression. Co-repressors that interact with nuclear receptors (and down-regulate gene expression) are also known. Co-activators are expressed at very low, limiting levels within a cell, thus transcription factors must compete for the limited amount of co-activators present. If an unmodified or modified ZPPAR4 combined with its corresponding ligand has a very strong affinity for limited co-activator(s), or if ZPPAR4 is overexpressed relative to other transcription factors, a ZPPAR4/ligand combination may significantly out-compete other transcription factor/ligand combinations for the limited co-activator(s). As a result, the ZPPAR4/ligand combination would essentially "turn off" target genes regulated by the non-ZPPAR4/ligand combinations. For a recent report describing nuclear receptor interactions with co-activators, including CBP, p300, and SRC-1 variants/p160, see Y. Kamei et al., *Cell* 85:403–14, 1996.

Melatonin is believed to be the natural ligand for the RZR/ROR family of NHRs. Thiazolidinediones have been reported to be high affinity, synthetic ligands that also bind to RZR/ROR (and PPAR7) nuclear hormone receptors. Thiazolidinediones act to increase insulin sensitivity in animal models of NIDDM, and related compounds are in clinical development as anti-diabetic agents. In general, thiazolidinediones and related compounds enhance the pleiotropic effects of insulin in all target tissues (for example, muscle, adipose and liver tissue) known to respond to the hormone. Improved insulin responsiveness is accompanied by reduced circulating levels of insulin and increased pancreatic stores of insulin. A concomitant increase in glucose transporter expression in target tissues has also been reported. Other reported effects of thiazolidinediones and related compounds (dependent on the presence of circulating insulin) include decreases in circulating glucose, triglycerides and cholesterol. See, generally, J. R. Colca and S. P. Tanis, in *Ann. Reports in Med. Chemistry*—27, Michne (ed.), Section IV, Chapter 23, Academic Press, 1992.

Thiazolidinediones also exhibit adipogenic effects on preadipocyte and mesenchymal stem cells in vitro, and PPARγ has been proposed as the target for these adipogenic effects. Elevated circulating lipid levels (another characteristic of NIDDM) have been reported to interfere with glucose disposal, and this alteration in lipid levels may be related to altered adipogenesis. Down-regulation of RZR/ROR or PPARγ receptors may contribute to elevated lipid levels and/or insulin resistance. Accordingly, thiazolidinediones may normalize the transcriptional activity of these types of receptors, including ZPPAR4. Thus, thiazolidinediones may, through direct or indirect interaction with ZPPAR4, modulate glucose metabolism in insulin-responsive tissues or influence adipogenesis.

Thiazolidinediones and RZR/ROR receptor activation have also been linked to anti-arthritic (autoimmune) activity, to hormone-dependent and—independent tumor inhibition activity, and to hormone-suppressive activity. Thus, many genes, including those involved in immunological, inflammatory, oncostatic, and hormonal responses, as well as genes involved in adipogenesis and glucose homeostasis, may be controlled via RZR/ROR receptors. Identification of the spectrum of genes that are regulated by thiazolidinedione/RZR/ROR receptor combinations can facilitate beneficial manipulation of genes having therapeutic value. For instance, agonists and antagonists of these receptors, including agonists and antagonists of ZPPAR4, may regulate or influence expression of one or more target genes of therapeutic value.

ZPPAR4 polypeptides may also be used within diagnostic systems for detection of circulating levels of ligand. Antibodies or other agents that specifically bind to ZPPAR4 may be used to detect the presence of receptor in tissue samples. Detection methods could be used as a diagnostic tool to monitor and quantitate receptor or ligand levels. Elevated or depressed levels of ligand or receptor may be indicative of pathological conditions, including cancers.

Fragments, domains or fusion polypeptides may also find use within the present invention. To facilitate purification of the receptor polypeptide, an N- or C-terminal extension, such as a poly-histidine tag, substance P, or a Flag™ peptide (Hopp et al., *Bio/Technology* 6:1204–10, 1988; available from Eastman Kodak Co., New Haven, Conn.), or another polypeptide or protein for which an antibody or other specific binding agent is available (such as maltose binding protein or immunoglobulin $F_c$ fragment), can be fused to the receptor polypeptide.

Ligand-binding ZPPAR4 polypeptide can be used for purification of ligand. ZPPAR4 polypeptide or a ligand-binding fragment thereof is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents, ions, or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) also may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see, Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

The cellular and/or in vivo expression of ZPPAR4 may be inhibited through use of anti-sense technology, ZPPAR4 knock-out technology or equivalent technology. By ablating the expression, and thus the function, of ZPPAR4, other cellular/in vivo moieties and actions may be altered and thus detected. Expression of ZPPAR4 in transgenic animals would facilitate analysis of the interaction(s) of ZPPAR4 with other cellular entities. Through use of such technologies (and appropriate polynucleotide delivery systems, if necessary), the physiological role(s) of ZPPAR4 may be dissected.

ZPPAR4 polypeptides can also be used to prepare antibodies that specifically bind to ZPPAR4 epitopes, peptides or polypeptides. Methods for preparing polyclonal and monoclonal antibodies are well known in the art (see, for example, Sambrook et al., *Molecular Cloning: A Laboratory Manual, Second Edition*, Cold Spring Harbor, N.Y., 1989; and Hurrell, J. G. R. (ed.), *Monoclonal Hybridoma Antibodies: Technigues and Applications*, CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a ZPPAR4 polypeptide may be increased through the use of an adjuvant, such as alum (aluminum hydroxide) or Freund's complete or incomplete adjuvant. Polypeptides useful for immunization also include fusion polypeptides, such as fusions of ZPPAR4 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to ZPPAR4 protein or peptide, and selection of antibody display libraries in phage or similar vectors (for instance, through use of immobilized or labeled ZPPAR4 protein or peptide).

Antibodies are defined to be specifically binding if they bind to a ZPPAR4 polypeptide with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to ZPPAR4 proteins or peptides. Exemplary assays are described in detail in *Antibodies: A Laboratory Manual*, Harlow and Lane (eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant ZPPAR4 protein or peptide.

Antibodies to ZPPAR4 may be used for tagging cells that express ZPPAR4; for isolating ZPPAR4 by affinity purification; for diagnostic assays for determining levels of ZPPAR4 polypeptides in tissues or cells; for detecting or quantitating ZPPAR4 as a marker of underlying pathology or disease; in analytical methods employing FACS; for screening expression libraries; for generating anti-idiotypic antibodies; and as neutralizing antibodies or as antagonists to block transcription in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anticomplement pairs as intermediates. Antibodies herein may also be directly or indirectly conjugated to drugs, toxins, radionuclides and the like, and these conjugates used for in vivo diagnostic or therapeutic applications.

The ZPPAR4 polynucleotides and/or ZPPAR4 receptor polypeptides disclosed herein may be useful as therapeutic targets, wherein agonists or antagonists could modulate one or more biological processes in cells, tissues and/or biological fluids. The ZPPAR4 polypeptides can be used to screen test samples for the presence of natural ligand, or of agonists or antagonists of the natural ligand. Additionally, the corresponding response elements recognized and bound by ZPPAR4 can be analyzed. The ZPPAR4 polynucleotide sequence can be used to obtain probes/oligonucleotides that can hybridize to counterpart sequences on individual chromosomes. Chromosomal identification and/or mapping of the ZPPAR4 gene will be a useful tool in determining disease association.

The invention is further illustrated by the following non-limiting examples.

EXAMPLES

Example 1

Identification of ZPPAR4 Polynucleotide

Oligonucleotide primers ZC10442 (antisense; SEQ ID NO:5) and ZC10443 (sense; SEQ ID NO:6) were designed from the sequence of an expressed sequence tag (EST) that was identified by homology to rat RZR and human ROR nuclear receptors. The primers were used for priming from the ends of the EST.

A cDNA library was prepared from human fetal brain poly A$^+$ RNA (Clontech Laboratories, Inc., Palo Alto, Calif.) using the protocol provided by the manufacturer. This cDNA was used as a template for polymerase chain reaction (PCR). Other libraries from which the EST could be amplified using the oligonucleotide primers (at an annealing temperature of 43° C. for 35 cycles) included heart, prostate, SaOS2 and bone marrow.

The conditions used for PCR were: 5 min at 94° C.; cycles of (94° C. for 30 sec; 55° C. for 30 sec; 72° C. for 1 min); followed by 7 min at 72° C. The amplified DNA was electrophoresed on a 1.2% low melting agarose gel and gel purified. The desired DNA fragment was 383 bp in length. The DNA fragment was purified using a QIAquick column (Qiagen Inc., Chatsworth, Calif.). Purified DNA was used in a ligation reaction using the pGEM-T (Promega, Madison, Wis.) vector system, according to the manufacturer's specification. The plasmid DNA was used to transform electro-competent DH10B *E. coli* cells by electroporation (ElectroMax™, GIBCO BRL, Gaithersburg, Md.).

Colonies were screened by PCR using EST-specific primers. Individual white colonies on LB-Amp/Meth/+IPTG+X-gal plates (representing recombinants) were picked and added to microcentrifuge tubes by swirling the toothpick with the colony on it in 50 µl $H_2O$. The cell suspension was heated to 99° C. for 5 min, then the suspension was centrifuged at 12,000×g for 2 min to remove cellular debris. Thereafter, 10 µl of the resultant colony supernatant was added to a tube containing 27 µl $H_2O$, 5 µl 10× Taq polymerase buffer (Clontech), 1.0 µl Taq polymerase (Clontech), 5 µl 2 mM dNTPs (Perkin Elmer Cetus, Norwalk, Conn.), 1.0 µl ZC10442 (SEQ ID NO:5) (20 pmol/µl), and 10 µl ZC10443 (SEQ ID NO:6) (20 pmol/µl). Amplification reactions were incubated at 94° C. for 1 min; and 25 cycles of (94° C. for 30 sec; 71° C. for 4 min). Products were analyzed by electrophoresis on a 0.9% agarose gel. Twelve white colonies out of 27 white possibles were screened, and nine colonies were positive. Of these, two colonies were cultured and used for sequencing. Plasmid templates were prepared for sequencing using a QIAwell™ 8 Plasmid Kit (Qiagen Inc.). The resultant sequence confirmed the 383 bp of the EST sequence, with the exception of 4/383 non-identical bases.

A 5' RACE (rapid amplification of cDNA ends) reaction was used to generate additional cDNA sequence. A human fetal brain "Marathon ready" cDNA library was prepared according to the manufacturer's instructions (Clontech), and used as template in a PCR reaction with oligonucleotide ZC10558 (SEQ ID NO:7) and the marathon primer AP-1 (Clontech). The PCR reaction was performed as follows: 1 min at 94° C.; and 25 cycles of (94° C. for 30 sec; 68° C. for 4 min). The reaction products were electrophoresed using a 0.9% agarose gel, and numerous bands were observed. The PCR reaction products were then used as a template for 5' nested RACE. Oligonucleotides ZC10559 (SEQ ID NO:8) and AP-2 (Clontech) were used in conjunction with 5' nested RACE to generate overlapping cDNA sequence. The 5' nested RACE PCR reaction was performed as follows: 1 min at 94° C.; and 25 cycles of (94° C. for 30 sec; 71° C. for 4 min). Upon electrophoresis, the 5' nested RACE reaction yielded a major band that migrated at about 700 bp on a 0.9% agarose gel, and minor bands migrating at about 800 and 1,000 bp. The 5' nested RACE reaction was repeated at a higher annealing temperature, using the previous 5' nested RACE product as template, and (a) AP-1 and ZC10559; (b) AP-2 and ZC10559; and (c) ZC10559. The PCR reactions were performed as follows: 5 min at 94° C.; and 25 cycles of (94° C. for 30 sec; 71° C. for 4 min). Electrophoresis of the PCR products revealed a single band at about 700 bp (slightly smaller with AP-2 than with AP-1). The 700 bp band was purified using QIAquick columns. Subsequent sequencing verified a 717 bp fragment.

A 3' RACE product was generated using the same "Marathon ready" human fetal brain cDNA library described above as template, and AP-1 (Clontech) and oligonucleotide ZC10555 (SEQ ID NO:9) as primers. Amplification and protocols for 3' RACE were performed as described for 5' RACE. The 3' RACE PCR reaction products were then used as a template for 3' nested RACE, using oligonucleotides ZC10556 (SEQ ID NO:10) and AP-2 (Clontech) to generate overlapping cDNA sequences (as described above for 5' nested RACE reactions). Upon electrophoresis, the 3' nested RACE reaction yielded a major band that migrated at about 1,700 bp on a 0.9% agarose gel, and minor bands migrating at about 600, 800, 900 and 1,000 bp. The 3' nested RACE reaction was repeated at a higher annealing temperature, using the previous 3' nested RACE product as template, and (a) AP-1 and ZC10556; (b) AP-2 and ZC10556; and (c) ZC10556. The PCR reactions were performed as follows: 5 min at 94° C.; and 25 cycles of (94° C. for 30 sec; 71° C. for 4 min). Electrophoresis of the PCR products revealed a predominant band at about 1,700 bp (slightly smaller with AP-2 than with AP-1). The 1,700 bp band was purified using QIAquick columns. Subsequent sequencing verified a 1380 bp fragment.

The 5' and 3' RACE fragments were combined with AP-2 oligonucleotides, and PCR was performed as described above for the RACE reactions. Subsequent sequencing of the resultant PCR product confirmed a 2094 bp full length clone.

Example 2

Tissue Distribution

Northern blots were performed using Human Multiple Tissue Blots (Clontech, Palo Alto, Calif.), and a human bone tissue blot. The 383 bp fragment described in Example 1 was used in conjunction with PCR and $^{32}$P-labeled dNTP to make a radiolabeled probe. EXPRESSHYB (Clontech) solution was used for prehybridization for 6 h at 42° C., and as a hybridizing solution for the Northern blots. Hybridization took place overnight at 42° C., and the blots were then washed once in 2×SSC+0.05% SDS at room temperature (RT), followed by two washes in 0.1×SSC+0.1% SDS at 50° C. Signal was detected in skeletal muscle only, with a transcript size of approximately 1.5 kb.

The 2094 bp full length fragment described in Example 1 was also made into a radiolabeled probe. Briefly, the full length fragment was radioactively labeled using a random priming MEGAPRIME DNA labeling system (Amersham, Arlington Heights, Ill.) according to the manufacturer's specifications. The probe was purified using a NUCTRAP push column (Stratagene Cloning Systems, La Jolla, Calif.). Prehybridization and hybridization were performed as described previously for the 383 bp PCR probe. Signal intensity was highest in heart, skeletal muscle and pancreas. Several transcript sizes were observed. In heart tissue, the predominant transcript was approximately 1.35 kb. In the pancreas, one high intensity band was localized at about 1.5 kb. In skeletal muscle, transcript sizes of about 1.2 kb, about 1.35 kb and about 4.2 were observed.

Example 3

PCR-Based Chromosomal Mapping of the ZPPAR4 Gene

The human ZPPAR4 gene is mapped by PCR using the Human/Rodent Somatic Cell Hybrid Mapping Panel Number 2 (National Institute of General Medical Sciences, Cornell Institute of Medical Research, Camden, N.J.). The panel consists of DNA isolated from 24 human/rodent somatic cell hybrids, each retaining one specific human chromosome and the parental DNAs. Specific ZPPAR4 gene oligonucleotide primers, ZC10442 (antisense; SEQ ID NO:5) and ZC10443 (sense; SEQ ID NO:6), are used for PCR amplification. A 50 µl PCR reaction mixture is then prepared containing 100 ng DNA template, 5 µl 10× KlenTaq PCR reaction buffer (Clontech), 4 µl dNTPs mix (2.5 mM each; Perkin-Elmer Cetus, Norwalk, Conn.), 50 pmol each ZC10442 and ZC10443, and 1 µl 50× Advantage KlenTaq Polymerase Mix (Clontech).

Example 4

Fluorescence In Situ Hybridization and Subchromosomal Mapping of the Human ZPPAR4 Gene The ZPPAR4 gene is mapped to a region of a specific chromosome using fluorescence in Situ hybridization as follows. A ZPPAR4-specific probe is prepared using nick translation. To a final volume of 50 µl is added 1 µg ZPPAR4-specific probe, 5 µl 10× nick translation buffer (0.5 M Tris/HCl, 50 mM MgCl$_2$, and 0.5 mg/ml BSA (nuclease free)), 5 µl dNTPs solution (0.5 mM dATP, 0.5 mM dGTP, and 0.5 mM dCTP), 5 µl 5 mM Bio-11-dUTP, 5 µl 100 mM DTT, 5 µl DNase I (1000× dilution of a 10 U/µl RNase-free stock; Boehringer Mannheim, Indianapolis, Ind.), and 12.5 U DNA polymerase I. The mix is then incubated at 15° C. for 1–2 h in a Boekel microcooler (Feasterville, Pa.). The reaction is terminated by addition of 5 µl 0.5 M EDTA, pH 7.4. The probe is purified using G-50 DNA purification spin columns (Worthington Biochemical Co., Freehold, N.J.) according the manufacturer's instructions.

Slide Preparation

Metaphase chromosomes are obtained from HEL cell culture. Cells are cultured in 100×15 mm culture dishes at 37° C., 50 CO$_2$. To prepare cells for harvest, 100 µl colemid (10 µl/ml stock; GIBCO BRL, Gaithersburg, Md.) is added to the culture medium and incubated at 37° C. for 2.5 to 3 h. The medium is then removed and transferred to a 15 ml conical tube. The cells are then rinsed with 2 ml 1×PBS (140 mM NaCl, 3 mM KCl, 8 mM Na$_2$HPO$_4$, 1.5 mM KH$_2$PO$_4$, pH 7.2), which is also added to the 15 ml conical tube. Cells are removed from the plate with 2 ml trypsin (GIBCO), added to the 15 ml conical tube, and centrifuged at 1,100 rpm for 8 min (Beckman, Palo Alto, Calif.; Model TJ-6 centrifuge, TH-4 swinging-bucket rotor). The supernatant is removed and the cells are resuspended in 8 ml 0.075 M KCl (prewarmed to 37° C.) and incubated in a 37° C. waterbath for 10 min. The cells are pelleted by centrifugation (Beckman TJ-J, TH-4 swinging bucket rotor) at 1,100 rpm for 5 min, and resuspended in 8 ml of cold methanol:acetic acid (3:1), added dropwise with mixing, to fix the cells. The cells are incubated at 4° C. for 20 min, followed by centrifugation (Beckman TJ-J, TH-4 swinging bucket rotor) at 1,100 rpm for 5 min. The fixation process is repeated two more times without the 4° C. incubation.

Frosted glass slides (VWR, Seattle, Wash.) are precleaned, and 5 µl 50% acetic acid is spotted on each slide, followed by 5 µl of the fixed cell suspension. The slides are allowed to air dry at room temperature, followed by incubation in a 42° C. oven overnight (Boekel). Cells are scored for suitable metaphase spreads using a microscope equipped with a phase contrast condenser.

In some cases, metaphase chromosome preparations are ASG (acetic/saline/giemsa) G-banded (Sumner et al., Nature New Biol. 232:31–32, 1971) with Gurr's improved R66 Giemsa's Stain (BDH Laboratory Supplies, Poole, England). Suitable G-band chromosomes are photographed prior to hybridization experiments as follows: Slides containing suitable chromosome preparations can be used at room temperature, or following a 45–60 min incubation at 90° C. Slides are then incubated for 2 h in 2×SSC (0.3 M NaCl, 0.03 M sodium citrate, pH 7.0), followed by a rinse in dH$_2$O, and stained in 5% Gurr's Giemsa stain diluted in 10% Gurr's Giemsa buffer solution, pH 6.8 (BDH Laboratory Supplies), prefiltered through Whatman #1 paper. G-banded metaphase chromosome spreads are visualized using an Olympus BH2-RFC microscope (Lake Success, N.Y.). To use the same metaphase chromosome spreads for hybridization experiments, the chromosomes are destained in 100% EtOH for 20 min and air dried.

Hybridization of Metaphase Chromosomes

To a 1.5 ml Eppendorf tube is added 2.5 to 5 µg human cot-1 DNA (GIBCO), 40–200 ng biotin labeled ZPPAR4- specific probe, 10–50 µg salmon testes DNA (Sigma Chemical Co., St. Louis, MO), 0.1 volume 3 M NaOAc and 2 volumes ethanol. This hybridization mix is vacuum dried in a Savant DNA SpeedVac DNA110 (Hicksville, N.Y.). The dried pellet is resuspended in 10 µl hybridization solution (10l dextran sulfate, 2×SSC, and 50% formamide (EM Science, Houston, Tex.)). The hybridization mix is denatured at 70–80° C. for 5 min, followed by cooling on ice and pre-annealing at 37° C. for 1–2 h. Chromosome spreads are denatured by immersing each slide in denaturing buffer (70% formamide, 2×SSC) at 70–80° C. for 5–10 min. The slides are then air dried at room temperature and prewarmed to 42° C. just prior to addition of 10 µl of hybridization solution. The chromosomes are then covered with a coverslip and incubated at 37° C. overnight in a moist chamber. The slides are then washed 3 times in 2×SSC containing 50% formamide at 42° C. for 5 min, followed by 3 washes in 2×SSC at 42° C. for 5 min, then one wash in 4×SSC containing 0.05% TWEEN-20 (Sigma) for 3 min at room temperature.

One hundred microliters of blocking buffer (4×SSC containing 5% non-fat dry milk) is added to each slide, which is then covered with a coverslip and incubated for 20 min at room temperature. The coverslip is removed and 100 µl of avidin/fluorescein (5 µg/ml fluorescein avidin DCS (cell sorter grade, Vector Laboratories, Inc., Burlingame, Calif.) in 4×SSC containing 0.05% TWEEN-20) is added, the slide covered with a coverslip and allowed to incubate for 20 min at room temperature. The slide is then washed 3 times in 4×SSC containing 0.05% TWEEN-20 at room temperature for 3 min, followed by addition of 100 µl anti-avidin (5 µg/ml biotinylated, affinity-purified goat anti-avidin D (Vector) in 4×SSC containing 5% non-fat milk). The slide is covered with a coverslip and incubated at room temperature for 20 min. The slides are washed as above, and a second fluorescein incubation is done using 100 µl avidin/fluorescein for 20 min at room temperature. In some cases, the avidin/fluorescein steps are repeated one additional time. The slides are then washed two times in 4×SSC containing 0.05% TWEEN-20 at room temperature for 3 min, followed by one wash in 1×PBS at room temperature for 3 min.

The slides are then mounted in anti-fade medium (9 parts glycerol containing 2% 1,4-diazobicyclo-(2,2,2)octane (DABCO) dissolved at 70° C., 1 part 0.2 M Tris/HCl, pH 7.5, and 0.25–0.5 µg/ml propidium iodide). The slides are viewed on an Olympus BH2-RFC microscope equipped with an Optronics ZVS-47E CCD RGB color video camera system (Goleta, Calif.). Images of the metaphase chromosome spreads are stored using Optimus software (Bothell, Wash.). Mapping of the ZPPAR4 probe is carried out using the fractional length (FL) method (Z) (Lichter et al., *Science* 247:64–69, 1990). Digitized images from the G-banded chromosomes are used in determining the corresponding FLqter values of the respective chromosome band boundaries with respect to the hybridized probe.

Alternatively, ZPPAR4 is mapped using the commercially available version of the Whitehead Institute/MIT Center for Genome Research's GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of ZPPAR4 with the GeneBridge 4 RH Panel, 25 µl reactions are set up in a PCRable 96-well microtiter plate (Stratagene, La Jolla, Calif.) and used in a RoboCycler Gradient 96 thermal cycler (Stratagene). Each of the 95 PCR reactions consists of 2.5 µl 10× KlenTaq PCR reaction buffer (CLONTECH Laboratories, Inc., Palo Alto, Calif.), 2 µl dNTPs mix (2.5 mM each, PERKIN-ELMER, Foster City, Calif.), 1.25 µl sense primer, ZC10443 (SEQ ID NO:6), 1.25 µl antisense primer, ZC110442 (SEQ ID NO:5), 2.5 µl RediLoad (Research Genetics, Inc., Huntsville, Ala.), 0.5 µl 50× ADVANTAGE KlenTaq Polymerase Mix (Clontech Laboratories, Inc.), 25 ng of DNA from an individual hybrid clone or control and ddH$_2$O for a total volume of 25 µl. The reactions are overlaid with an equal amount of mineral oil and sealed. The PCR cycler conditions are as follows: an initial 1 cycle 4 minute denaturation at 94° C., 35 cycles of a 1 minute denaturation at 94° C., 1.5 minute annealing at 65° C. and 1.5 minute extension at 72° C., followed by a final 1 cycle extension of 7 minutes at 72° C. The reactions are separated by electrophoresis on a 3% NuSieve® GTG agarose gel (FMC Bioproducts, Rockland, Me.).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polypeptide consisting of the amino acid sequence from amino acid residue 216 to amino acid residue 469 of SEQ ID NO:2.

2. An isolated polypeptide consisting of the amino acid sequence from amino acid residue 216 to amino acid residue 674 of SEQ ID NO:2.

* * * * *